United States Patent
Semprevivo

(10) Patent No.: US 6,428,793 B1
(45) Date of Patent: Aug. 6, 2002

(54) LIPOGLYCAN COMPOSITIONS AND METHODS OF TREATING PARASITIC INFECTIONS

(75) Inventor: Lloyd H. Semprevivo, Wendell, MA (US)

(73) Assignee: University of Massachusetts, Boston, MA (US)

(*) Notice: Subject to any disclaimer, the term of this patent is extended or adjusted under 35 U.S.C. 154(b) by 0 days.

(21) Appl. No.: 09/523,404

(22) Filed: Mar. 10, 2000

Related U.S. Application Data

(60) Provisional application No. 60/123,931, filed on Mar. 12, 1999.

(51) Int. Cl.[7] .......................... A61K 39/00; A21D 2/00; A23L 1/27; G01N 33/53; G01N 33/569
(52) U.S. Cl. ................ 424/265.1; 426/178.1; 426/184.1; 426/9; 426/265.1; 435/7.1; 435/7.22; 435/975
(58) Field of Search .................. 435/7.22, 7.1, 435/975; 426/178.1, 184.1, 265.1, 9.1; 424/265.1

(56) References Cited

U.S. PATENT DOCUMENTS 5,212,298 A 5/1993 Rademacher et al. ...... 536/55.2
5,280,113 A 1/1994 Rademacher et al. ...... 536/55.2
5,679,347 A 10/1997 Porcelli et al. .......... 424/184.1
6,261,788 B1 * 7/2001 Cummings et al. ........ 435/7.22

OTHER PUBLICATIONS

Bergwerff et al., "The immunologically reactive part of immunopurified circulating anodic antigen from *Schistoma mansoni*—", *The Journal of Biological Chemistry*, (1994), vol. 269, No. 50, pp. 3151031517.*
Cummings et al., "Glycobiology of schistosomiasis", *FASEB Journal*, (1996), vol. 10, pp. 838–848.*
Turco et al., "Expression of an . . . ," The Journal of Biological Chemistry, 259:3883–3889, 1984.
Radin, Norman S., "Extraction of Tissue . . . ," Methods in Enzymology, 72:5–7, 1981.
Semprevivo, Lloyd H., "An improved method for . . . ," Carbohydrate Research, 177:222–227, 1988.

* cited by examiner

*Primary Examiner*—W. Gary Jones
*Assistant Examiner*—Arun K. Chakrabarti
(74) *Attorney, Agent, or Firm*—Fish & Richardson P.C.

(57) ABSTRACT

A composition for and a method of eliciting in a vertebrate a protective immune response against an eukaryotic parasite are disclosed. The method includes administering to the vertebrate a composition having a carrier group coupled to an oligosaccharide obtained from a lipoglycan found on the surface of an eukaryote. The composition is administered in an amount sufficient to elicit a protective immune response against the parasite.

17 Claims, No Drawings

LIPOGLYCAN COMPOSITIONS AND METHODS OF TREATING PARASITIC INFECTIONS

CROSS REFERENCE TO RELATE APPLICATION

This application claims priority from U.S. Provisional Application Serial No. 60/123,931, filed Mar. 12, 1999, now abandoned.

FIELD OF THE INVENTION

The invention relates to carbohydrate chemistry and vaccinology.

BACKGROUND OF THE INVENTION

Parasites of animals and humans pose a worldwide problem. For example, schistosomiasis, after malaria, is the most common cause of human morbidity and mortality. Approximately 600 million people are at risk for schistosome flatworm infection, and approximately 200 million people in 74 countries are infected. Twenty million people (mostly children) have a severe form of the disease, and 200,000 die annually from the disease.

Mammalian parasites, such as platyhelminths of the genus Fasciola or Schistosome and protozoans of the genus Trichomonas, can avoid immune elimination and survive for months or years in the fully immunocompetent vertebrate host. The surface of these parasites elicits a T cell-independent immune response characterized by the predominant production of IgM antibodies but fails to induce a T cell-independent response characterized by the production of IgG, IgE, and IgA isotype antibodies.

The production of IgG (as well as IgE and IgA) and their binding to the exterior of a pathogen is generally required for antibody-dependent cell-mediated cytotoxicity, a mechanism demonstrated to be effective in destroying parasitic worms. The binding of thymus-dependent antibodies (IgG, IgE, and IgA) to the exterior of extracellular pathogens is also generally required for phagocytosis by host macrophages and other immune functions included in a process of immune activation called "opsonization". Opsonization is an immune mechanism frequently associated with destruction of extracellular protozoan parasites. It is generally believed that several mammalian parasites evade immune elimination by failing to induce surface-specific T cell-dependent functions, such as IgG, IgE, and IgA production.

SUMMARY OF THE INVENTION

The invention is based on the isolation of new lipoglycans from the surface of platyhelminths. These lipoglycans, as well as those isolated from certain protozoan parasites, can be used in compositions for inhibiting, treating, or diagnosing parasitic infection.

Accordingly, the invention features a method of eliciting in a vertebrate a protective immune response (e.g., one including a T cell-dependent antibody response) against an eukaryotic parasite by administering to the vertebrate a composition containing a carrier group coupled to an oligosaccharide (or a mixture of oligosaccharides) obtained from a lipoglycan found on the surface of an eukaryote. The composition is administered in an amount sufficient to elicit a protective immune response against the eukaryotic parasite.

The oligosaccharide can be isolated or obtained from a lipoglycan (i.e., a molecule having at least one lipid group and at least one carbohydrate group) having a molecular weight of about 180 kilodaltons. In addition, the lipoglycan includes at least one lipid group and at least one carbohydrate group. For example, the lipoglycan can include a lipid group, one or more fucose groups, three to five galactoseamine groups per fucose group, two to four glucosamine groups per fucose group, one to two galactose groups per fucose group, one to two glucose groups per fucose group, one to two rhamnose groups per fucose group, and one to three mannose groups per fucose group. Alternatively, the lipoglycan can include a lipid group, one or more fucose groups, three to five galactoseamine groups per fucose group, seven to eleven glucoseamine groups per fucose group, three to five galactose groups per fucose group, one to two glucose groups per fucose group, and three to five mannose groups per fucose group.

The eukaryote can be a protozoan or an adult platyhelminth (e.g., of the genus Schistosoma or Fasciola, or of the class cestoidea). The eukaryotic parasite can be a protozoan or a pathogenic platyhelminth (e.g., of the genus Schistosoma or Fasciola, or of the class cestoidea).

The carrier group can be coupled to the oligosaccharide by a linker (e.g., 2-(4-amino-phenyl)ethylamine).

The invention also includes an isolated lipoglycan (e.g., one about 180 kDa in size) including a lipid group, one or more fucose groups, three to five galactoseamine groups per fucose group, two to four glucoseamine groups per fucose group, one to two galactose groups per fucose group, one to two glucose groups per fucose group, one to two rhamnose groups per fucose group, and one to three mannose groups per fucose group. In a specific embodiment, this lipoglycan includes, per each fucose group, four galactosamine groups, three glucosamine groups, two galactose groups, two glucose groups, and two mannose groups. The lipoglycan can be obtained from a species of the genus Schistosoma.

The invention further includes an isolated lipoglycan (e.g., one about 180 kDa in size) having a lipid group, one or more fucose groups, three to five galactoseamine groups per fucose group, seven to eleven glucoseamine groups per fucose group, three to five galactose groups per fucose group, one to two glucose groups per fucose group, and three to five mannose groups per fucose group. In a specific embodiment, the lipoglycan includes, per each fucose group, four galactosamine groups, nine glucosamine groups, four galactose groups, one glucose group, and four mannose groups. This lipoglycan can be obtained from a species of the genus Fasciola and/or contain inositol.

The invention further includes a composition including a carrier group coupled to an oligosaccharide isolated from the lipoglycans of the invention. The carrier group can be coupled to the oligosaccharide by a linker (e.g., 2-(4-aminophenyl)ethylamine).

A lipoglycan is a molecule that contains at least one lipid group and at least one carbohydrate group. An isolated lipoglycan is a preparation of a lipoglycan of a particular molecular weight that is at least 60% by weight of the lipoglycan of interest. Of course, the lipoglycan can be isolated and purified to higher levels of purity, e.g., at least 80%, 90%, or 95%, of a composition is the desired lipoglycan. The other 40% can include other macromolecules, such as lipids, proteins, carbohydrates, and lipoglycans not of that particular molecular weight. The lipoglycan can be free of naturally occurring amino acid residues. The molecular weight of a lipoglycan is determined by sodium dodecyl sulfate-polyacrylamide gel electrophoresis (SDS-PAGE) under reducing conditions.

As used herein, "protective immune response" means an immune response capable of preventing, reducing, or inhibiting productive infection by a parasite. In the case of a prophylactic composition, the animal or human host has not been infected, thus the composition prevents or inhibits (partially or completely) any productive infection or one or more symptoms of productive infection caused by a subsequent exposure to a parasite. In the case of a therapeutic composition, the animal or human host exhibits an on-going productive infection, and the composition reduces or ends a productive infection. A productive infection is one in which viable parasites can be isolated from a host. A protective immune response includes IgG antibody production and T cell activation. A protective composition, e.g., a vaccine, elicits a protective immune response.

A carrier group is a molecule which, when coupled to an oligosaccharide, helps present the oligosaccharide antigen to a mammalian immune system. Examples of carrier groups include proteins, such as bovine serum albumin (BSA), tetanus toxoid, ovalbumin, and parasite protein.

An adjuvant is a substance that is incorporated into or is administered simultaneously with the compositions of the invention. Adjuvants increase the duration or level of the immune response in an animal after administration of an antigen. An adjuvant can also facilitate delivery of an antigen into the animal or into specific tissues, cells, or locations throughout the body of the animal. Examples of adjuvants include, but are not limited to, incomplete Freund's, complete Freund's, and alum; and can contain squalene (e.g., MF59, Chiron Corp, Emeryville, Calif.), monophospholipid A (e.g., DetoxJ, Ribi ImmunoChem Research, Inc., Hamilton, Mont.), saponins (QS-21, Cambridge Biotech, Cambridge, Mass.), non-ionic surfactants (NISV, Proteus, Cheshire, United Kingdom), tocols (U.S. Pat. No. 5,667,784), biodegradable-biocompatible poly(D, L-lactide-co-glycolide) (U.S. Pat. No. 5,417,986), immune-stimulating complexes (ISCOMs), and/or liposomes.

A non-reducing end group, as it pertains to a sugar, means a sugar that does not reduce Benedict's reagent in the Benedict's test for reducing sugars; see, e.g., http://www.acp.edu/web/genchem/thedisk/food/bened/bened.htm)

The new isolated lipoglycans are useful in producing therapeutic and prophylactic compositions, such as protective vaccines, against parasites. In turn, the compositions are useful in eliciting a protective immune response against a parasite as detailed in the methods of the invention.

The isolated lipoglycans, compositions, and methods of the invention provide a novel means of preparing and using vaccines against a wide variety of eukaryotic parasites such as flatworms and protozoans. Unlike many parasites in natural infection, the various aspects of the invention offer the ability to stimulate T cell-dependent immune responses in an animal or human host, including parasite-specific IgG production. The methods and compositions of the invention can be used to raise lipoglycan-specific antibodies useful in diagnosis of infection. The isolated lipoglycans of the invention also can be used in diagnostic assays in which the lipoglycans of the invention bind to antibodies present in a biological sample.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The invention provides new therapeutic and prophylactic compositions for use in treating parasitic infections, e.g., by eliciting a protective immune response against parasites. Many parasites are not immunogenic, or not sufficiently immunogenic to produce an effective immune response. The methods of the invention offer a parasite antigen presentation strategy that produces a protective immune response. This strategy includes isolating a lipoglycan from the parasite surface, preparing oligosaccharides from the lipoglycan, coupling the oligosaccharides to a carrier group, and administering the oligosaccharide/carrier group conjugate to the mammal to be vaccinated. These vaccinations offer protective immunity by, at least in part, inducing parasite-specific IgG production, as detailed in the Examples below.

The methods, lipoglycans, and compositions of the invention can be used to vaccinate a mammal against a variety of parasites. One general class of parasites are worms belonging to the phylum platyhelminthes. Platyhelminths include parasitic flatworms of the class trematoda (e.g., worms of the genus Schistosoma, such as *S. bovis, S. indicum, S. japonicum, S. mattheei, S. spindale, S. haematobium, S. intercalatum, S. mansoni,* or *S. mekongi;* worms of the genus Fasciola, such as *F. hepatica, F. gigantica,* and *F. jacksoni;* and the worm *Fascioloides magna*) that infect humans and farm animals. Platyhelminths also include tapeworms of the class cestoidea, which infect humans (worms of the genus Taenia) or dogs (worms of the genus Mesocestoides). Another general class of parasites are protozoans such as those of the genus Trichomonas, Tritrichomonas, Leishmania, or Entamoeba. *Trichomonas vaginalis* is particularly prevalent in the U.S. and can cause symptomatic genitourinary tract infections.

General procedures for isolating the lipoglycans, using the compositions, and performing the methods of the invention, are described below.

Isolation of Lipoglycans from Parasites

Parasites are generally available from vendors, such as the American Type Culture Collection (ATCC), Rockville, Md. For example, *T. vaginalis* is available as Cat. No. 30001 from ATCC. In addition, *F. hepatica* matacercariae can be purchased from Baldwin Enterprises, Monmouth, Oreg., or isolated from aquatic snails, a natural host of the parasite. Parasites are also obtainable from various research laboratories, including those supported by the World Health Organization. Alternatively, they can be isolated from natural hosts or the environment (e.g., Fasciola from abattoirs or Fascioloides from deer experiment stations in the field).

The preparation of a parasite at various stages of its life cycles is known in the art. For example, *F. hepatica* newly excysted juveniles (NEJ) can be isolated according to Hanna, Exp. Parasitol., 50:103–114, 1980. More mature worms can generally be isolated according to Gibbs et al., The Veterinary Clinics of North America: Food Animal Practice, Vol. 2, W.B. Saunders Co., Philadelphia, Pa., pp. 261–275, 1996.

Lipoglycans can be isolated from a parasite by methods known in the art. Typically, the parasites are washed with phosphate-buffered saline.(PBS), and then the low molecular weight lipids on the surface of the parasite, including simple and complex lipids, can be extracted by organic solvents. These crude low molecular weight lipids, which include glycerophospholipids, glycoglycerolipids, and sphingolipids, can be extracted with a solution of chloroform/methanol/water (3:2:1) as described in Turco et al., J. Biol. Chem., 259:3883–3889, 1984; and Bennett, Parasitol., 77:325–332, 1978. Alternatively, the crude lipids can be extracted with a solution of hexane/isopropanol (3:2) as described in Radin, Meth. Enzymol., 72:5–7, 1981.

The choice of extraction method will depend on the parasite. For example, lipoglycan from *Fasciola hepatica* can be isolated by pre-treatment of parasite tissue using either the chloroform/methanol/water or the hexane/isopropanol extraction method (see Example 1 below) to differentially remove low molecular weight lipids. On the other hand, the lipoglycan from *Schistosoma mansoni* cannot be isolated using chloroform/methanol/water solvent. However, these low molecular weight lipids can be differentially extracted using the hexane/isopropanol method (see Example 2 below). The extraction with chloroform/methanol/water or hexane/isopropanol in the case of *Fasciola hepatica*, or hexane/isopropanol in the case of *Schistosoma mansoni* leaves a residue from which lipoglycan can be extracted with solvent E.

The lipoglycan can be isolated from the low molecular weight lipid residue by extraction with a solution of water, ethanol, diethylether, pyridine, and $NH_4OH$ (15:15:5:1:0.017), also called solvent E, as described in Turco et al., supra. The solvent E extract is dried to isolate the lipoglycan. Additional procedures can be performed to further purify the lipoglycan, such as gel filtration, hydrophobic chromatography, and methanol precipitation.

The isolated lipoglycans can be characterized by using SDS-PAGE to determine their molecular weights. In addition, a monosaccharide profile for the carbohydrate portion of the lipoglycan can be obtained by subjecting the lipoglycan to acid hydrolysis and analysis on a high performance anion exchange chromatography system fitted with a pulsed amperometric detector using the manufacturer's instructions. Such systems and detectors are available from Dionex, Inc., Sunnyvale, Calif.

Producing Oligosaccharide/Carrier Group Conjugates

To produce an antigen useful in a therapeutic or prophylactic composition, such as an anti-parasite vaccine, oligosaccharides are released from the isolated lipoglycan. This can be done using, e.g., standard mild acid hydrolysis or glycosidase treatment. See, e.g., Semprevivo, Carbohy. Res., 177:222–227, 1988. Additional purification (e.g., by column chromatography) of the oligosaccharides can be performed to isolate oligosaccharides of a specific size range (e.g., 800–3000 daltons). These oligosaccharides can include non-reducing end groups, repeating subunits, and/or core portions of the lipoglycan. In addition, the oligosaccharides obtained from a particular LG are expected to contain the same carbohydrate residues as in the LG itself.

The oligosaccharides or mixture of oligosaccharides are then coupled to a carrier group by conventional methods to form effective immunogens because, as haptens, the oligosaccharides alone are likely to be poor immunogens. Carrier groups can be any polypeptide, organic polymer, or smaller molecule that is suitable for administration to a mammal. When coupled to the oligosaccharides, the carrier groups enhance presentation of oligosaccharide epitopes to a mammalian immune system, thereby inducing an immune response specific for the oligosaccharides and, by extension, for the lipoglycan on the surface of the parasite. The use of a mixture of many different oligosaccharides helps to prevent the target eukaryote from adapting and avoiding the immune response.

Any standard chemical linker (e.g., a bi-functional linker containing, for example, reactive amino groups) can be used to couple the oligosaccharides to the carrier group. Examples of such linkers include 1-cyano-4-dimethylaminopyridinium tetrafluoroborate, 4-(4-N-maleimidomethyl)cyclohexane-1-carboxyl hydrazide, and a phenethylamine-isothiocyanate derivative. See, e.g., Lee et al., Vaccine, 14:190–198, 1996; Ragupathi et al., Glycoconjugate J., 15:217–221, 1998; Roy et al., Canad. J. Biochem. Cell Biol., 62:270–275, 1984; and Smith et al., Methods Enzymol., 50:169–171, 1978.

Chemistry and techniques suitable for coupling oligosaccharides to a carrier group such as BSA are known in the art. For example, the carbonyl group of the terminal reducing monosaccharide residue of an oligosaccharide can react with the primary alkylamine group of a linker such as 2-(4-aminophenyl)ethylamine to form an intermediate. This intermediate is then reduced with sodium borohydride to form an unstable intermediate and to facilitate a condensation between the terminal arylamino group of the linker portion of the intermediate and a diazo bridge to residues, e.g., lysine residues, of a polypeptide carrier such as BSA. See, e.g., Zopf et al., Meth. Enzymol., 50:163–169, 1978; and Semprevivo, supra.

While different oligosaccharide molecules derived from the digestion of a single lipoglycan source are coupled to the carrier group using the above methods, oligosaccharides from more than one lipoglycan (e.g., lipoglycans from two species of parasites) also can be linked to a single carrier group. Such multi-specific conjugates are especially useful for the production of broadly protective vaccines.

Preparation of Compositions Containing Oligosaccharide/Carrier Group Conjugates

The compositions can include one or more different types of oligosaccharide/carrier group conjugates. For example, conjugates produced from different lipoglycans can be mixed together in the same composition to produce a cross-protective vaccine composition. In general, the vaccine compositions can be prophylactic (for uninfected individuals) or therapeutic (for individuals already infected).

The compositions optionally include a pharmaceutically acceptable excipient, such as the diluent phosphate buffered saline or bicarbonate (e.g., 0.24 M $NaHCO_3$). The excipients used in the new compositions can be chosen by one of ordinary skill in the art, on the basis of the mode and route of administration, and standard pharmaceutical practice, without undue experimentation. Suitable pharmaceutical excipients and diluents, as well as pharmaceutical necessities for their use, are described, e.g., in Remington's Pharmaceutical Sciences. An adjuvant, e.g., a cholera toxin, *Escherichia coli* heat-labile enterotoxin (LT), liposome, or immune-stimulating complex (ISCOM), can also be included in the vaccine compositions.

To formulate the therapeutic compositions, the oligosaccharide/carrier group conjugates can be further purified by standard methods to remove contaminants such as endotoxins, if present. The final conjugate preparation can be lyophilized and resuspended in sterile, deionized water. Appropriate pharmaceutical excipients can then be added.

The therapeutic compositions can be formulated as a solution, suspension, suppository, tablet, granules, powder, capsules, ointment, or cream. In the preparation of these compositions, at least one pharmaceutical excipient can be included. Examples of pharmaceutical excipients include solvent (e.g., water or physiological saline), solubilizing agent (e.g., ethanol, polysorbates, or Cremophor EL7), agent for achieving isotonicity, preservative, antioxidizing agent, lactose, starch, crystalline cellulose, mannitol, maltose, calcium hydrogen phosphate, light silicic acid anhydride, calcium carbonate, binder (e.g., starch, polyvinylpyrrolidone, hydroxypropyl cellulose, ethyl cellulose, carboxy methyl cellulose, or gum arabic), lubricant (e.g., magnesium stearate, talc, or hardened oils), or stabilizer (e.g., lactose, mannitol, maltose, polysorbates, macrogols, or polyoxyethylene hardened castor oils). If desired, glycerin, dimethylacetamide, 70% sodium lactate, surfactant, or basic substance such as sodium hydroxide, ethylenediamine, ethanolamine, sodium bicarbonate, arginine, meglumine, or trisaminomethane can be added. Biodegradable polymers such as poly-D,L-lactide-co-glycolide or polyglycolide can be used as a bulk matrix if slow release of the composition is desired (see e.g., U.S. Pat. Nos. 5,417,986, 4,675,381, and 4,450,150). Pharmaceutical preparations such as solutions, tablets, granules or capsules can be formed with these components. If the composition is administered orally, flavorings and/or colors can be added.

Administration of Compositions Containing Oligosaccharide/Carrier Group Conjugates The new compositions can be administered via any appropriate route, e.g., intravenously, intraarterially, topically, by injection, intraperitoneally, intrapleurally, orally, subcutaneously, intramuscularly, sublingually, nasally, by inhalation, intraepidermally, or rectally.

Dosages administered in practicing the invention will depend on factors including the specific vaccine antigen and its concentration in the composition, whether an adjuvant is co-administered with the antigen, the type of adjuvant co-administered, the mode and frequency of administration, and the desired effect (e.g., protection from infection or treatment of an existing infection). Suitable dosages as can be determined by one skilled in the art without undue experimentation. In general, the new compositions can be administered in amounts ranging between 0.01 $\mu$g and 1 mg of the conjugate per kilogram body weight. If adjuvants are administered with the compositions, amounts of only 1% of the dosages given immediately above can be used. The dosage range for veterinary use can be adjusted according to body weight.

Administration is repeated as necessary, as determined by one skilled in the art. For example, in prophylaxis a priming dose can be followed by three booster doses at weekly intervals. A booster shot can be given at 8 to 12 weeks after the first immunization, and a second booster can be given at 16 to 20 weeks, using the same formulation. Sera or T-cells can be taken from the individual for testing the immune response elicited by the composition against the parasite (or parasite surface antigens) in vitro. Methods of assaying antibodies, cytotoxic T-cells, or other mediators of immune function against a specific antigen and assaying their ability to kill parasites in vitro are well known in the art, including the ones described in the Examples below. See also, e.g., U.S. Pat. No. 4,656,033; WO 90/02563; Vieira et al., Comp. Biochem. Physiol., 100B:507–516, 1991; Butterworth et al., Immunol. Res., 61:5–39, 1982; Bickle et al., J. Immunol., 128:2101–2106, 1982; and Simpson et al., Infect. Immun., 41:591–597, 1983. Additional boosters can be given as needed. By varying the amount of the immunogen or composition, the immunization protocol can be optimized for eliciting a maximal immune response.

Before administering the above compositions in humans, toxicity and efficacy testing can be conducted in animals. In an example of efficacy testing, mice can be vaccinated via an oral or parenteral route with a composition containing a oligosaccharide/carrier group conjugate antigen. After the initial vaccination or after optional booster vaccinations, the mice (and corresponding control mice receiving mock vaccinations) are challenged with a $LD_{95}$ dose of the parasite. Protective immunity is then determined by an absence or reduction (e.g., a 70%, 80%, 90%, 95%, 99%, or 100% reduction) in the number of viable parasites. Alternatively, the challenge is a lethal dose, and protective immunity is determined by an absence of lethality. In general, a lethal Fasciola dose in mice is five or more cysts, and a lethal schistosome dose in mice is about 50 or more cercariae.

For example, oligosaccharides from a schistosome lipoglycan can be conjugated to BSA, diluted in PBS, and delivered into mice. As a control, a non-specific oligosaccharide (e.g., maltotriose) can be conjugated to BSA, diluted in PBS, and delivered into mice on the same day. A booster vaccination is give about one month after the first vaccination. About two weeks later, the mice are challenged with 50 to 500 *Schistosoma mansoni* cercariae. The mice are sacrificed and necropsied about a week after challenge, and the number of viable lung-stage worms in each mouse counted. Protective immunity is conferred by the absence or reduction in number of viable worms in the test mice compared to the presence of viable worms in the control mice. Additional details regarding schistosome infection animal models can be found in Sher et al., J. Inf. Dis. 130:626–633, 1974; and Bergquist et al., Parasitol. Today 14:99–104, 1998.

A vaccine based on a Fasciola lipoglycan oligosaccharide/carrier group conjugate can be tested in like manner as for the schistosome vaccine described above, except that the timing of various steps are adjusted as necessary, and the liver, not the lungs, of sacrificed mice are examined for signs of infection. Again, protective immunity is conferred by the absence or reduction in total number of viable worms in the test mice compared to the presence of viable worms in the control mice, or as a reduction in a symptom associated with infection. Additional details regarding Fasciola infection animal models can be found in Morrison et al., Vaccine 14:1603–1612. 1996; Hughes et al., Res. Vet. Sci. 30:93–98, 1981; and Rajasekariah et al., Exp. Parasitol. 44:233–238, 1978.

Details regarding protozoan infection animal models can be found in Corbeil, Parasitol. Today 10:103–106, 1994; Ghadirian et al., Parasite Immunol. 7:479–487, 1985; Farrell, Exp. Parasitol. 40:89–94, 1976; and Gorczynski, Cell. Immunol. 94:1–10, 1985.

The dose of the conjugate administered to a subject will depend generally upon the severity of the condition (if any), age, weight, sex, and general health of the subject.

Physicians, pharmacologists, and other skilled artisans are able to determine the most therapeutically effective treatment regimen, which will vary from patient to patient. The potency of a specific composition and its duration of action can require administration on an infrequent basis, including administration in an implant made from a polymer that allows slow release of the conjugate. Skilled artisans are also aware that the treatment regimen must be commensurate with issues of safety and possible toxic effect produced by the conjugate or other components in the compositions, such as adjuvants.

Variations

The portions of the lipoglycan molecule which induce protective antibodies can be determined by raising monoclonal antibodies specific for specific regions of the lipoglycan and determining which of these portions of the lipoglycan participate in parasite destruction or elimination. In general, antibodies can be raised by injecting into an animal the immunogenic compositions described herein. Monoclonal antibodies and hybridomas producing them can be cloned and screened (using the original antigen complex as the capture moiety) from a B cell population isolated from the immunized animals using standard methods in the art of molecular biology.

Once antibodies are selected using these screens, the specific oligosaccharide structures to which they bind can be identified by at least two methods. In the first method, the antibodies are used to screen a library of oligosaccharide molecules, each member of the library having a known chemical structure. In the second method, the antibodies are used to "fish out" the specific oligosaccharides from a complex mixture of oligosaccharides produced by digesting a lipoglycan using the methods described herein. The structure of the specific oligosaccharides are then identified by chromatographic, spectrometric, or other physical and/or chemical methods known in the art of carbohydrate chemistry.

Another variation involves the selection of carrier groups. Infection with a parasite typically induces specific humoral and cellular immune responses in a host. However, parasite proteins by themselves seldom induce significant resistance to homologous challenge. These parasite proteins therefore can provide ideal carriers to which lipoglycan oligosaccharides can be conjugated. Those proteins which elicit an immune response early in infection can function as efficacious carrier groups for inducing resistance to infection.

The means of conjugating oligosaccharides to carrier groups can also be improved. Several procedures and linkers are available with which to facilitate conjugation of carbohydrates to carrier molecules, as described above.

EXAMPLES

The invention will be further described in the following examples, which do not limit the scope or content of the invention in any way.

Example 1

A Protective Vaccine Against Fasciola

Whether *Fasciola hepatica* is able to avoid host immune responses by limiting the response to IgM antibody production was first examined.

Lipoglycan Isolation

To isolate a lipoglycan useful for producing a vaccine against parasites, *F. hepatica* adults were processed by standard methods to remove gut contents (Lang et al., J. Parasitol. 63:1046–1049, 1977) and then flash frozen. Immediately after harvesting from the host, the adult flukes were washed in excess sterile phosphate buffered saline (pH 7.2) at about 37° C. to 38° C. for 30 minutes, followed by a second wash in the same solution for 20 minutes. The *F. hepatica* carcass, including surface coat, was treated initially by delipidizing the surface coat isopropanol/hexane (2:3) as described in Radin, supra, followed by extraction with solvent E as described in Turco et al., supra. The extract was dried under a stream of dry nitrogen, yielding a residue.

In a separate experiment, it was determined that a chloroform/methanol/water (1.0:1.0:0.3) extraction, as described in Turco et al., supra, in place of the isopropanol/hexane extraction, could also be used to delipidize the surface coat prior to solvent E treatment to extract the lipoglycan.

The solvent E residue was resuspended in 40 mM ammonium hydroxide and analyzed by: 1) the orcinol-sulfuric acid procedure as modified in White et al., Oligosaccharides, Chapter 2, In: Carbohydrate Analysis, A Practical Approach. (Chaplin et al., eds.), IRL Press Ltd., Oxford, p. 38., 1986; and 2) by Peterson's modification of the micro Lowry method to quantitate protein (Yamamoto et al., Lipid, 5:442, 1970) using a commercially available kit (Sigma Catalog No. P 5656). These analyses indicated that the solvent E extract contained about 0.5 mg of carbohydrate per 1 g of tissue. Trace amounts of protein were detected.

The solvent E residue was further purified by gel filtration on a Sepharose CL-4B column (Pharmacia). The CL-4B column (2.5×40 cm) was eluted with a solution containing 40 mM ammonium hydroxide and 1 mM EDTA, and the $OD_{490}$ readings of each fraction were monitored. Peak fractions 12 through 33 were pooled and applied to a hydrophobic octyl Sepharose column equilibrated with a solution containing 0.1 M ammonium acetate and 5% n-propanol. The octyl Sepharose column (Pharmacia) was eluted with n-propanol (5–60% gradient), and the $OD_{490}$ again monitored. Additional details on the above isolation procedure can be found in Singh et al., J. Biol. Chem., 269:21972–21982, 1994. The lipoglycan in the peak fractions from the octyl Sepharose column was isolated by methanol precipitation.

Lipoglycan Structure

To estimate the size of the *F. hepatica* lipoglycan, the isolated lipoglycan was subjected to reducing SDS-PAGE on a 12% gel. Carbohydrate bands in the gel were visualized using periodic acid-Schiffs reagent, revealing a set of tightly spaced bands about 180 kDa in size. Coomassie blue staining of the gel failed to detect any protein in the isolated lipoglycan preparation.

To determine the monosaccharide composition of the lipoglycan, the preparation was subjected to mild acid hydrolysis by incubating. About 225 µg of lipoglycan was treated with 2 ml of 2.5 N trifluoroacetic acid at 100° C. for 3 hours (Singh, Mol. Biochem. Parasitol. 57:281–294, 1993). This treatment non-specifically cleaves glycosidic linkages in the carbohydrate component of the lipoglycan. The resulting monosaccharides were then analyzed on a high performance anion exchange system fitted with a pulsed amperometric detector (Dionex, Inc., Sunnyvale, Calif.) as described in Hardy et al., Proc. Nat. Acad. Sci. USA, 85:3289–3293, 1988. The lipoglycan samples were hydrolyzed using 2.5 N trifluoroacetic acid, as described above, in 13×100-mm screw cap Pyrex tubes. The caps were sealed with teflon seals. The tubes were cooled and the acid removed by rotary evaporation at about 40° C. The samples were then dissolved in 15 mM NaOH and applied to a Carbopac-PA1 column using 15 mM NaOH as eluant. The monosaccharide composition was determined by high performance anion exchange chromatography using a pulsed amperometric detector (Dionex Corp., Sunnyvale, Calif.). Specific monosaccharides were identified by comparing experimental retention times with those of similarly treated monosaccharides controls, which were purchased from Sigma. The molar ratios were determined by integrating the area under the chromatographic peaks representing specific sugars.

The analysis revealed that the lipoglycan contained fucose, galactosamine, glucosamine, galactose, glucose, and mannose in the ratio 1.0:4.0:9.0:4.0:1.0:3.8.

The identity of the terminal monosaccharides in the lipoglycan was revealed by digesting the lipoglycan with β-galactosidase, α-fucosidase, and α-mannosidase (Oxford Biosystems). The released monosaccharides were identified by the high performance anion exchange system described above. The digestions revealed that terminal β-1,4-linked galactose, terminal α-fucose, and terminal α-mannose residues were components of the lipoglycan. The β-1,4-galactose linkage was confirmed by lectin-binding.

The β-1,4-galactose linkage was confirmed using immobilized ricin lectin. The lipoglycan radiolabeled with galactose oxidase/NaB[$^3$H]$_4$ was applied to a column (1×2 cm) of Ricinus communis agglutinin-1 (RCA-1). RCA-1 lectin covalently linked to an agarose bead (EY Laboratories, Inc.) equilibrated with PBS, pH 7.4. The loaded column was first washed with PBS and then with 0.2 M lactose. PBS containing 0.1% Triton X-100 was used to flush the column. Fractions (1.2 ml) were collected and measured for radioactivity. The lipoglycan (LG) was retained on the column and released only by the solution containing lactose, confirming the presence of the β-1,4-galactose linkage.

These data indicated that the carbohydrate component of the F. hepatica lipoglycan includes a branched polysaccharide having different terminal monosaccharides.

The phosphorus content of the lipoglycan was also determined. The lipoglycan was subjected to perchloric digestion and subsequent analysis according to Barlett, J. Biol. Chem., 234:466–468, 1959.

A micro adaptation of the method described in Fiske et al., J. Biol. Chem. 66:375, 1925, as modified by Barlett, J. Biol. Chem. 234:466–468, 1959, was used to detect phosphorus in Fasciola and Schistosoma LG. In this procedure, dried parasite LG was dissolved in 100 μl of 10 N H$_2$SO$_4$ and heated to 160° C. for three hours. All subsequent reagents were added at ⅕ the volume or mass indicated by Barlett, supra. The results were read at 830 nm, with phosphorus content determined using a standard curve developed using sodium dihydrogen phosphate.

Two hundred micrograms of dried fluke LG was utilized in the quantitative phosphate detection procedure described in Bartlett, supra. The experiment demonstrated that 200 femtograms of fluke LG contained approximately 0.1 femtograms of phosphorus. These results suggest that several phosphorus residues are present in each fluke LG molecule, but that the glycan portion of the molecule does not have repeated phosphodiester groups as found in the LG of protozoa. The phosphodiester bonds between sugar groups, as found in protozoan LG, results in the extreme lability of these molecules to mild acid conditions. The ratio of phosphorus to carbohydrate in protozoan LG is about 1:3 (Singh et al., J. Biol. Chem. 269:21972–21982, 1994).

The finding that fluke LG is not especially susceptible to mild acid hydrolysis and that the ratio of phosphorus to carbohydrate in this molecule is also low suggests that fluke LG does not contain phosphodiester bonds between carbohydrate groups. This finding is consistent with the other experiments that found that the lipoglycan was not degraded by mild acid hydrolysis (at 40 mM trifluoroacetic acid) or by nitrous acid deamination.

Whether inositol was a constituent of the F. hepatica lipoglycan, thereby indicating that the lipoglycan exists as a glycosylphosphatidylinositol (GPI)-anchored molecule on the surface of the adult worm, was examined. The lipoglycan was labeled with $^3$H by standard procedures and then treated with phospholipase C (Oxford GlycoSystems, Inc. Rosedale, N.Y.) to remove inositol residues, if any. $^3$H-labeled LG was obtained by reducing LG molecules previously treated with galactose-oxidase (Boehringer Mannheim Biochemica) with NaB[$^3$H]$_4$ (New England Nuclear) (Gahmber et al., J. Biol. Chem. 248:4311–4317, 1973). The digest, and separately an undigested labeled control lipoglycan, was passed into a phenyl-Sepharose column (Pharmacia), followed by elutions using an aqueous solution containing 0.1 N acetic acid and 0.1 M NaCl and, separately, solvent E. Radiolabeled material from the digested sample was eluted in the aqueous elution, while radiolabeled material from the control sample was eluted only in the organic elution. The radiolabeled material eluting in the aqueous phase was confirmed to be inositol by gas/liquid chromatography as described in Singh et al., J. Biol. Chem., 269:21972–21982, 1994; and Singh, Mol. Biochem. Parasitol., 57:281–294, 1993.

F. hepatica Vaccine Composition

To determine whether oligosaccharides derived from the isolated F. hepatica lipoglycan might serve as an effective immunogen, the lipoglycan was subjected to mild trifluoroacetolysis and to derivatization with 2-(4-aminophenyl) ethylamine as described in Semprevivo, supra. The derivatized intermediate was then coupled to BSA to form the oligosaccharide/BSA conjugate as described in Semprevivo, supra.

The isolated oligosaccharide/BSA conjugate was examined by SDS-PAGE and Western blot. Before conjugation, a BSA control sample exhibited a molecular weight of about 67,000 daltons and was immunologically detectable with a commercially available anti-BSA antibody. The conjugate, however, exhibited a faster gel mobility and could be detected with serum antibodies from a F. hepatica-infected rat as well as with the anti-BSA antibody, as expected.

Maltotriose (Sigma Catalog No. M 8378) was conjugated to BSA according to the above procedure to form a negative control conjugate.

The F. hepatica vaccine composition was completed upon mixing the lipoglycan oligosaccharide conjugate with a aluminum hydroxide gel (Malox). The aluminum hydroxide gel is an adjuvant suitable for use in humans and is often referred to as alum.

Validating a Rodent Model

As a positive control experiment for the vaccination experiment described below, five-week old male Wistar rats were inoculated orally with 10 F. hepatica metacercariae, challenged 7 weeks later with 20 metacercariae, and exsanguinated a week after challenge. Immune serum from each F. hepatica-infected rat was obtained by the method described in Hanna, supra. Sera were also obtained from F. hepatica-infected rats, mice, sheep, and cattle.

The class of antibody present in each serum sample was determined by indirect immunofluorescence. The target for the assay was living F. hepatica NEJ. The NEJ was mixed with each of the serum samples to allow binding between the serum antibodies and the NEJ. Serum antibody-bound NEJ were then incubated with goat fluorescein-labeled IgM-specific or IgG-specific secondary antibodies (Kirkegaard & Perry Laboratories, Inc., Gaithersburg, Md.). The secondary antibody corresponded to the relevant species from which the serum was isolated. The dilutions of secondary antibodies were about 1:200 to 1:300. After incubation with the secondary antibody, the NEJs were examined under a fluorescence microscope. Intense fluorescence was observed on NEJs treated with IgM-specific secondary antibodies, but not with IgG-specific secondary antibodies. This result indicated that, as expected, mammals infected with F. hepatica were unable to mount a T cell-dependent immune response that included production of beneficial IgG antibodies.

Vaccination of Rodents

For the vaccination experiment, mature female rats (Wistar strain, Charles River Laboratories) and mature female mice (CD1 strain, Charles River Laboratories) were each vaccinated with oligosaccharide and maltotriose conjugates. The dose per rat was 40 µg of conjugate in 0.4 ml of alum. The dose per mouse was 20 µg of conjugate in 0.2 ml of alum. Some animals were vaccinated with alum only, as an additional negative control. This study utilized 15 mice and 15 rats, with five rats and five mice receiving the lipoglycan oligosaccharide/BSA conjugate, five rats and five mice receiving the maltotriose/BSA conjugate, and five rats and five mice receiving alum only. Thirty days post-vaccination, the animals received either a homologous booster of 5 µg of conjugate mixed in 0.1 ml alum or alum only, depending on the initial vaccination. Sera was recovered from each animal one day pre-vaccination and 40 days post-vaccination.

Challenging Vaccinated Rodents

Healthy F. hepatica metacercariae were selected with the aid of a dissecting microscope to insure consistent challenge infections of vaccinated animals. Only those metacercarial cysts with defined interior morphology indicating viable larvae were selected for challenge. Forty days after vaccination, each animal was orally inoculated with three (for mice) or five (for rats) F. hepatica metacercariae. The animals were sacrificed and necropsied 30 days post-infection. The liver was dissected from each animal and examined for living worms by visual inspection under a dissecting scope and for signs of worm-induced disease, e.g., liver inflammation or liver necrosis. The livers of mice receiving the alum or maltotriose negative controls had an average of 2.4 flatworms per liver and exhibited inflammation and necrosis. The livers of mice receiving the F. hepatica lipoglycan oligosaccharide/BSA conjugate revealed no worms and no inflammation or necrosis. Similar results were obtained in rats, except that the livers of negative control rats had an average of 4.6 flatworms per liver. No worms were found in the livers of rats vaccinated with the F. hepatica lipoglycan oligosaccharide/BSA conjugate.

To confirm that the immunogenicity was due to the lipoglycan oligosaccharide/BSA conjugate, a series of control vaccinations were carried out as described above, except that the vaccine compositions contained isolated lipoglycan, lipoglycan oligosaccharides, or lipoglycan oligosaccharide/BSA conjugate that had been treated with periodate to degrade complex carbohydrates to monosaccharide units. It was known that under periodate treatment, carbohydrate residues containing glycol groups are oxidized to dialdehydes, but if three adjacent carbon each contain hydroxyl groups, formic acid is produced from the opening of sugar rings, thereby destroying the configuration of the sugars.

Rats receiving each of these vaccine compositions in the same manner as described above were never protected from challenge with F. hepatica. This result indicated that (1) the lipoglycan alone cannot elicit a protective immune response, (2) the oligosaccharides derived from the lipoglycan alone cannot elicit a protective immune response, and (3) the protective immune response conferred by the oligosaccharide/BSA conjugate is dependent on the complex structure of the oligosaccharides.

Evaluating Sera from Vaccinated Rats

Sera from rats vaccinated with the F. hepatica oligosaccharide/BSA conjugate vaccine were tested for their ability to react with and/or kill living worms in vitro. F. hepatica NEJs or 30 day post-infection liver flukes isolated from mice were used as targets.

Indirect immunofluorescence, performed as described above, was used to determine reactivity. Staged liver flukes were separately reared for 5 days in Medium 199 (Sigma) supplemented with 15% pre-immune rat serum. F. hepatica NEJs or 30 day post-infection liver flukes were then separately incubated in either (1) undiluted rat pre-immune serum; (2) serum isolated from rat, mouse, cow, or sheep infected with F. hepatica; (3) sera from rats vaccinated with the maltotriose/BSA conjugate; or (4) sera from rats vaccinated with the F. hepatica oligosaccharide/BSA conjugate. Sera were diluted between 100-fold and 1000-fold in media prior to contact with F. hepatica worms.

NEJs exposed to either rat pre-immune sera or sera from the maltotriose/BSA-vaccinated rats appeared healthy and unchanged. NEJs incubated in any one of the sera from F. hepatica-infected animals exhibited visible surface coat precipitates resulting from IgM antibody complexes. Though able to form such complexes, these sera were unable to kill either NEJs or 30 day post-infection liver flukes in vitro.

In contrast, sera from rats vaccinated with the oligosaccharide/BSA conjugate killed F. hepatica NEJs and 30 day post-infection liver flukes. The sera's cytopathic effect was confirmed by the worms' physical features, such as rounding up, development of surface coat blebs, and loss of integument. Optical microscopes were used to detect ultrastructural defects, such as blebs. An electron microscope was used to detect the loss of integument. Critically, the worms were not viable (i.e., dead or dying) after incubating with these sera. Thus, even though the protective F. hepatica vaccine included oligosaccharides originally isolated from only adult worms, sera from vaccinated animals also killed juvenile worms. This result indicated that, whatever humoral immune response was being elicited by the oligosaccharide/BSA conjugate, the response elicited was effective against both the juvenile and adult stages of the worms.

To confirm that the in vitro killing by sera was dependent on antibodies specific for complex oligosaccharide structures, rather than dependent on antibody binding to simple monosaccharide units, the following experiment was performed. The carbohydrates of the F. hepatica lipoglycan were reduced to individual monosaccharide units as described above. The monosaccharides were then added to the serum/worm incubations to achieve a concentration of 100 µm monosaccharide. The ability of the sera to kill worms was not affected, indicating that the killing activity was not due to antibody binding to simple monosaccharide units on the surface of the worm.

The class of antibody in sera from vaccinated rats was determined as described above. The results indicated that IgG antibodies, rather than IgM antibodies, predominated in these sera.

Long-Term Protection

To determine whether the oligosaccharide/BSA conjugate vaccine provided long-term protection, sera were collected from five vaccinated rats over a period of three years. Each serum was tested against F. hepatica NEJs as described above. The killing capacity and reactivity of the sera did not decline over the course of three years. In addition, the vaccinated rats did not exhibit a shortened life span and appeared healthy during the same period of time, suggesting little or no toxicity associated with the vaccine.

Cross-Protection

To test whether the oligosaccharide/BSA conjugate derived from a F. hepatica lipoglycan was capable of providing cross-protection against other species, sera from vaccinated rats were tested against juvenile Fasciola magna worms as described above for F. hepatica worms. F. magna juvenile flatworms treated with serum from a vaccinated rat rounded-up and died within several days. Control sera (e.g., from maltotriose/BSA conjugate-vaccinated rats) did not affect F. magna viability. These results indicated that the vaccine composition containing F. hepatica lipoglycan oligosaccharide/BSA conjugate is capable of eliciting cross-protective immunity against species other than the species of origin of the lipoglycan.

It was also observed that the IgG antibodies found in the sera of vaccinated rats could bind to an isolated lipoglycan molecule found on the surface of platyhelminth Schistosoma mansoni (described in Example 2 below), as shown by Western blotting. This suggested that the degree of cross-protection could be broad enough to encompass protection against a platyhelminth of a different genus.

The results described in Example 1 provided a reasonable basis to assume that an F. hepatica vaccine as prepared above and administered in proportion to body weight would protect farm animals such as cattle from a new productive infection with F. hepatica and related worms. In addition, these results indicated that, if the above vaccine would be able to induce an IgG response in already infected cattle, such cattle could clear a pre-existing productive infection.

Example 2

A Protective Vaccine Against Schistosoma

To determine whether the vaccine strategy described in Example 1 could also be used for other less related platyhelminths, a lipoglycan was isolated from Schistosoma mansoni using the procedure described in Example 1. In a separate experiment, it was observed that replacement of the isopropanol/hexane extraction with the chloroform/methanol/water extraction as described in Turco et al., supra, in the isolation procedure could not be used to isolate the S. mansoni lipoglycan. This lipoglycan was estimated to be about 180 kDa when examined by reducing SDS-PAGE and ran as a single band on a SDS-PAGE gel. The S. mansoni lipoglycan isolate was free of other periodic acid-Schiff's species and free of any detectable protein.

A monosaccharide analysis of the carbohydrate component of the S. mansoni lipoglycan was performed as described in Example 1. These results were then compared to carbohydrate analysis using gas chromatography and mass spectrometry. The analysis indicated that the lipoglycan contained fucose, and that, for each fucose residue, the lipoglycan contained 4 galactosamine residues, 3.1 glucosamine residues, 1.84 galactose residues, 1.84 glucose residues, 1.45 rhamnose residues, and 2.17 mannose residues.

Oligosaccharides were digested from the S. mansoni lipoglycan and conjugated to BSA as described in Example 1. In addition, the oligosaccharides were conjugated to tetanus toxoid (SSI-TetanusTox; Accurate Chemical and Scientific Corp.) as the carrier using the procedure described for the BSA conjugation in Example 1. Vaccine compositions containing the oligosaccharide conjugates were produced as previously described. Controls were produced by mixing only BSA with alum or only tetanus toxoid with alum.

Mice were initially injected with vaccine and control compositions in the quantities specified in Example 1. At 28 days post-initial inoculation a booster was given as described in Example 1. At 38 days post-initial inoculation, mice were challenged with S. mansoni cercariae. Mice that were immunized with adult lipoglycan oligosaccharide conjugated to tetanus toxoid were challenged 200 cercariae per mouse. Mice that were immunized with adult lipoglycan oligosaccharide conjugated to BSA were challenged with 100 cercariae per mouse. Each of the four groups of five animals received BSA, oligosaccharide/BSA conjugate, tetanus toxoid, or oligosaccharide/tetanus toxoid conjugate, respectively.

Six days post-challenge, the mice were sacrificed and necropsied. The lungs from each animal were removed, and the worms were counted and examined. The lungs of mice receiving BSA contained an average of 20.2 worms per animal, while the lungs of mice receiving oligosaccharide/BSA conjugate contained an average of 5.5 worms per animal. More important than this 73% reduction in worm count was the observation that all worms found in the lungs of vaccinated mice were dead or dying, while all worms found in the lungs of control mice were healthy and motile.

The lungs of mice receiving tetanus toxoid contained an average of 30.9 worms per animal, while the lungs of mice receiving oligosaccharide/tetanus toxoid conjugate contained an average of 3.9 worms per animal. Again, more important than this 88% reduction in worm count was the observation that all worms found in the lungs of vaccinated mice were dead or dying, while all worms found in the lungs of control mice were healthy and motile. The use of tetanus toxoid as the carrier also indicated that the vaccine composition could encompass oligosaccharides conjugated to a variety of carrier molecules.

To reconfirm the protective immunity conferred by the S. mansoni lipoglycan oligosaccharide-tetanus toxoid conjugate, a second vaccination/challenge experiment was conducted using the procedures described immediately above. The reduction of worm counts in this second experiment was 89%, thereby confirming that the protective immunity elicited by this vaccine is reproducible between separate experiments.

The survival and health of vaccinated versus unvaccinated animals after challenge with S. mansoni was also examined. Five mice were vaccinated with lipoglycan-tetanus toxoid conjugate vaccine using the protocols described above. Five more mice served as unvaccinated controls. The vaccinated mice were boosted once at 28 days post-vaccination (initial), and all 10 mice were challenged percutaneously with 100 virulent cercariae 93 days post-vaccination.

The time to moribund status, if achieved, for each animal was then determined. These mice were observed daily for general appearance and condition. By day 50 post-infection, all unvaccinated mice were characterized by lethargy or otherwise appeared ill. One mouse of the control group died on day 55 post-infection, another on day 57 post-infection. The remaining three mice were obviously moribund by day 58 post-infection and were sacrificed to prevent suffering. Upon necropsy, all of the control mice were found to have heavy parasite liver egg burdens.

In contrast, all vaccinated mice were alive and exhibited no ill effects 101 days after challenge. These results indicated that these vaccinated mice were not subject to the pathologic effects associated with massive parasite egg deposition, supporting the conclusion that the challenge parasite burden was killed and/or prevented from successful egg deposition.

Thus, protection was shown by the dramatic reduction in the number of worms in vaccinated animals, as well as by the elimination of any observable symptoms, including death, typically elicited by *S. mansoni* infection. In addition, all of the worms isolated from the vaccinated animals were dead or dying (i.e., not viable).

These results, combined with those of Example 1, indicated that a second (BSA conjugate) and third (tetanus conjugate) protective vaccine against a platyhelminth could be produced. Because the mouse model of schistosome infection is known by those skilled in the field to be reasonably predictive of human efficacy, the results described in this Example also provide a reasonable foundation to conclude that the *S. mansoni* vaccine described herein would, when administered proportionally to body weight, protect humans from schistosome infection (i.e., schistosomiasis).

Example 3

Vaccines Against Protozoans

Surface lipoglycans were isolated from human protozoan pathogens *Leishmania donovani, Leishmania tropica, Trichomonas vaginalis,* and *Tritrichomonas foetus* following the procedure described in Example 1.

To determine whether individuals infected with each of these protozoans produced an IgM or IgG antibody response, the protozoan lipoglycans were each immobilized onto a nitrocellulose membrane in a dot blot format. The lipoglycans were then exposed to sera obtained from individuals infected with each of the protozoans under conditions sufficient to allow binding of serum antibodies to the immobilized lipoglycans. Two micrograms of lipoglycan dissolved in 3 $\mu$l of solvent E were blotted on a polyvinylidene difluoride (PVDF) membrane (BioRad, Hercules, Calif.) forming a circle about 3 mm in diameter. The level of IgG or IgM binding to the lipoglycans were then determined using an alkaline phosphatase-labeled anti-human IgM or anti-human IgG antibody. After development of a phosphatase-converted chromogenic reagent, it was observed that serum antibodies binding to the isolated lipoglycans were predominantly IgM. Thus, these protozoans failed to induce a beneficial IgG response, as observed in Example 1 in animals infected with *F. hepatica.*

Groups of 5 mice were inoculated with each protozoan LG conjugate vaccine (20 femtograms/mouse), and other groups of 5 mice were inoculated with each of the isolated LGs (20 femtograms/mouse). A single group of 5 mice was inoculated with BSA (20 femtograms/mouse) only. All mice were boosted 28 days later with 10 femtograms of the same material that they had received initially. Serum was collected at day 27 and 35 post-immunization. Mice inoculated with isolated LG frequently developed no specific antibody response or had a weak IgM response. Mice immunized with the LG-oligosaccharide-protein conjugate vaccines had a dominant IgM response at day 27 but a dominant IgG response at day 35. Mice inoculated with BSA did not develop anti-LG antibody responses.

This result, in light of the results in Examples 1 and 2, indicated that the vaccine strategy leading to protective immunity against platyhelminths was also useful for protozoans.

OTHER EMBODIMENTS

It is to be understood that while the invention has been described in conjunction with the detailed description thereof, the foregoing description is intended to illustrate and not limit the scope of the invention, which is defined by the scope of the claims. Other aspects, advantages, and modifications are within the scope of the following claims.

For example, the procedures described above are applicable to other platyhelminths. The structure of the tegument of all platyhelminths, including aspidobothreams, monogeneans, digeneans, and cestodes is structured according to a common plan (Mehlhorn et al., Parasitology in Focus, Facts and Trends, Springer Verlag, N.Y., pp 238–240, 1988). This observation suggests that all parasitic flatworms may avoid immune elimination by having a coat of lipoglycan on their surface. In conjunction with the teachings described herein, a vaccine composed of specific platyhelminth surface lipoglycan oligosaccharides coupled to a protein carrier can induce protective immunity. A conjugate or anti-idiotype can be prepared for the specific LG of a variety of eukaryotic parasites.

Therefore, protection against any eukaryotic parasite can be achieved by the methods and compositions of the invention. Eukaryotic parasites amenable to the protection conferred by the methods of the invention include the following: (1) digenetic trematodes, which are serious pathogens of man and domestic animals including but not limited to the following (*Fasciolopsis buski, Dicrocoelium dendriticum, Paragonimus westermani,* and *Clonorchis sinensis*); (2) monogenean flatworm parasites, which infect fish; and (3) cestode (tapeworm) parasites.

Of particular interest is the development of vaccines against *Taenia solium, Echinococcus granulosus,* and *Echinococcus multilocularis*. Vaccine for these parasites will be against the adult stage in humans, in the first case, and in canines in the latter two.

Other parasites that can be protected against include the malaria parasite. Complex carbohydrates frequently function as T-independent type 2 (TI-2) antigen. Antigens of this type induce T-independent immune responses that result in late developing, primarily IgM-type responses that lack immune memory. Malaria typically induces an immunity that may be slow to develop, involves increase in IgM antibody, and fades within a year leaving the victim susceptible to a new infection the following year. Using the present disclosure, it can be determine which of the larger carbohydrate-rich glycoconjugates of mammalian stage malarial forms induce predominantly IgM responses. It is then possible to reduce these glycoconjugates to oligosaccharide subunits. Using the procedures described above, the oligosaccharides can then be conjugated to a protein carrier as a means of inducing a T cell-dependent immune response to the specific carbohydrates. To validate the approach, vaccinated animals can be challenged with virulent homologous parasites to establish the protective capacity of the vaccine molecule. This approach, will be successful for all members of the family Apicomplexa, to which the malaria parasite belongs.

Protective immune responses against nematodes can also be produced by the methods and compositions of the invention. The gut of nematodes is lined with a single layer of cells, which have Golgi bodies and membrane bound inclusions. The gut is protected on the luminal side by a loosely bound layer of amorphous material (Mehlhorn et al., Parasitology in Focus, Facts and Trends, Chapter 3, Springer-Verlag, N.Y., 1988). This situation is reminiscent of the surface of parasitic flatworms. Using the procedures described herein, the material composing the loosely bound layer can be isolated and used to produce an oligosaccharide conjugate vaccine. Such a vaccine can be used to vaccinate hosts against round worm infection, especially members of the family Trichostongylidae, members of which are serious pathogens of domestic stock animals.

Anti-idiotype vaccines are also included in the invention. The production of high avidity anti-LG monoclonal antibodies are made possible by the methods and compositions of the invention. Known monoclonal antibody (mAb) technology can be used to make large amounts of anti-idiotype (anti-id) against the V region (idiotype) of an antibody of proven protective value using standard techniques. Protective value of a specific antibody can be established using in vitro incubation procedures in which living parasites are suspended in various concentrations of antibody and viability of the parasite is monitored over time. Protection is measured by passive transfer of specific monoclonals into susceptible hosts followed by challenge with the homologous virulent parasite, e.g., as described in this disclosure. The capacity of the antibody to kill the living mammalian host would be considered the best evidence of a mAb's therapeutic or prophylactic value. This procedure is particularly relevant to those situations in which the LG of a particular eukaryotic parasite is difficult or expensive to obtain.

What is claimed is:

1. An isolated lipoglycan comprising a lipid group, one or more fucose groups, three to five galactoseamine groups per fucose group, two to four glucoseamine groups per fucose group, one to two galactose groups per fucose group, one to two glucose groups per fucose group, one to two rhamnose groups per fucose group, and one to three mannose groups per fucose group.

2. The lipoglycan of claim 1, wherein the lipoglycan has a molecular weight of about 180 kilodaltons.

3. The lipoglycan of claim 1, wherein the lipoglycan comprises, per each fucose group, four galactosamine groups, three glucosamine groups, two galactose groups, two glucose groups, one to two rhamnose groups, and two mannose groups.

4. The lipoglycan of claim 1, wherein the lipoglycan is obtained from a species of the genus Schistosoma.

5. A composition comprising a carrier group coupled to an oligosaccharide obtained from the lipoglycan of claim 1.

6. The composition of claim 5, wherein the carrier group is coupled to the oligosaccharide by a linker.

7. The composition of claim 6, wherein the linker is 2-(42-aminophenyl)ethylamine.

8. An isolated lipoglycan comprising a lipid group, one or more fucose groups, three to five galactoseamine groups per fucose group, seven to eleven glucoseamine groups per fucose group, three to five galactose groups per fucose group, one to two glucose groups per fucose group, and three to five mannose groups per fucose group.

9. The lipoglycan of claim 8, wherein the lipoglycan has a molecular weight of about 180 kilodaltons.

10. The lipoglycan of claim 8, wherein the lipoglycan comprises, per each fucose group, four galactosamine groups, nine glucosamine groups, four galactose groups, one glucose group, and four mannose groups.

11. The lipoglycan of claim 8, wherein the lipoglycan is obtained from a species of the genus Fasciola.

12. The lipoglycan of claim 8, further comprising inositol.

13. A composition comprising a carrier group coupled to an oligosaccharide obtained from the lipoglycan of claim 8.

14. The composition of claim 13, wherein the carrier group is coupled to the oligosaccharide by a linker.

15. The composition of claim 14, wherein the linker is 2-(4-aminophenyl)ethylamine.

16. The composition of claim 5, wherein the mixture of oligosaccharides comprises oligosaccharides having a molecular weight of from 800 to 3000 daltons.

17. The composition of claim 13, wherein the mixture of oligosaccharides comprises oligosaccharides having a molecular weight of from 800 to 3000 daltons.

* * * * *